(12) United States Patent
Nakamura et al.

(10) Patent No.: US 7,161,044 B2
(45) Date of Patent: Jan. 9, 2007

(54) CATALYTIC GAS PHASE OXIDATION REACTION

(75) Inventors: Daisuke Nakamura, Himeji (JP); Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/958,015

(22) Filed: Oct. 4, 2004

(65) Prior Publication Data

US 2005/0090695 A1    Apr. 28, 2005

(30) Foreign Application Priority Data

Oct. 22, 2003 (JP) ............................. 2003-362599
Apr. 9, 2004 (JP) ............................. 2004-115946

(51) Int. Cl.
C07C 45/27 (2006.01)
C07C 51/10 (2006.01)
C07C 51/14 (2006.01)
C07C 51/16 (2006.01)

(52) U.S. Cl. .................. 568/476; 568/478; 568/479; 562/518; 562/521; 562/535

(58) Field of Classification Search ............... 568/476, 568/478, 479; 562/518, 521, 535
See application file for complete search history.

(56) References Cited

U.S. PATENT DOCUMENTS

| 3,801,634 | A | | 4/1974 | Krabetz et al. | |
|---|---|---|---|---|---|
| 4,873,368 | A | | 10/1989 | Kadowaki et al. | |
| 5,198,581 | A | | 3/1993 | Kawajiri et al. | |
| 5,276,178 | A | * | 1/1994 | Onodera et al. | ............ 562/537 |
| 5,719,318 | A | | 2/1998 | Kawajiri et al. | |
| 6,399,818 | B1 | | 6/2002 | Tanimoto et al. | |
| 6,410,786 | B1 | * | 6/2002 | Onodera et al. | ............ 562/535 |
| 6,563,000 | B1 | | 5/2003 | Yunoki et al. | |
| 6,632,965 | B1 | * | 10/2003 | Tanimoto et al. | ............ 562/535 |
| 6,657,080 | B1 | * | 12/2003 | Yunoki | ..................... 562/535 |

FOREIGN PATENT DOCUMENTS

| CN | 1055914 A | 11/1991 |
|---|---|---|
| CN | 1210511 A | 3/1999 |
| EP | 0 450 596 A2 | 10/1991 |
| EP | 1 055 662 A1 | 11/2000 |
| EP | 1 460 053 A1 | 9/2004 |
| EP | 1 466 883 A1 | 10/2004 |
| JP | 53-30688 | 8/1978 |
| JP | 4-217932 A | 8/1992 |
| JP | 7-10802 A | 1/1995 |
| JP | 7-84400 B2 | 9/1995 |
| JP | 9-241209 A | 9/1997 |
| JP | 2000-336060 A | 12/2000 |
| JP | 2001-328951 A | 11/2001 |
| WO | WO 98/24746 A1 | 6/1998 |

* cited by examiner

*Primary Examiner*—Sikarl A. Witherspoon

(57) ABSTRACT

An object of the present invention is to provide a catalytic gas phase oxidation reaction in which: even under reaction conditions of a higher gas pressure, a higher concentration of the raw material gas and a larger space velocity of a reaction gas, the thermal accumulation at the hot spot portion can be sufficiently suppressed with ease and at low costs, so that the reaction can be continued for a long time while a high yield is maintained. As a means of achieving this object, a catalytic gas phase oxidation reaction according to the present invention is a catalytic gas phase oxidation reaction with molecular oxygen or a molecular-oxygen-containing gas by using a fixed-bed multitubular reactor packed with catalysts; with the catalytic gas phase oxidation reaction being characterized in that: a catalyst-packed layer of each reaction tube of the reactor is divided into at least two reaction zones in a tubular axial direction; and the packing of the catalysts is such that the occupation volumes of the catalysts differ between at least two of the reaction zones and that an inert substance molding is mixed in at least one of the reaction zones.

12 Claims, No Drawings

CATALYTIC GAS PHASE OXIDATION REACTION

BACKGROUND OF THE INVENTION

A. Technical Field

The present invention relates to a catalytic gas phase oxidation reaction. Specifically, the present invention relates to a catalytic gas phase oxidation reaction with molecular oxygen or a molecular-oxygen-containing gas by using a fixed-bed multitubular reactor packed with catalysts.

B. Background Art

In cases where, in the catalytic gas phase oxidation reactions with the molecular oxygen or the molecular-oxygen-containing gas by using the fixed-bed multitubular reactor packed with catalysts, (A) at least one compound selected from the group consisting of propylene, isobutylene, t-butyl alcohol, and methyl t-butyl ether is used as a raw material to produce an unsaturated aldehyde corresponding to the raw material, (B) an unsaturated aldehyde is used as a raw material to produce an unsaturated carboxylic acid corresponding to the raw material, and (C) at least one compound selected from the group consisting of propylene, isobutylene, t-butyl alcohol, and methyl t-butyl ether is used as a raw material to produce an unsaturated carboxylic acid corresponding to the raw material, then these catalytic gas phase oxidation reactions are accompanied with extremely exothermic reactions, so a local portion having an extraordinarily high temperature (which may hereinafter be referred to as "hot spot portion") occurs in a catalyst layer.

When the hot spot portion has a high temperature, the catalyst excessively causes the oxidation reaction at this hot spot portion, thus lowering the yield of the objective product, and, in the worst case, the catalyst causes a runaway reaction. A catalyst as located at the hot spot portion is exposed to the high temperature, and therefore there is accelerated the deterioration of the catalyst, such as changes of physical properties and chemical properties of the catalyst to result in lowering its activity and the selectivity of the objective product. Particularly, in the case of a molybdenum-containing catalyst (e.g. a molybdenum-bismuth-iron-containing catalyst, a molybdenum-vanadium-containing catalyst; hereinafter the same), the composition and properties of the catalyst tend to change due to sublimation of the molybdenum component, and therefore the deterioration extent of the catalyst is large.

The above problems are more striking in the case of carrying out the reaction with the gas pressure (hereinafter, the gas pressure refers to a "gas pressure at the gas outlet of each reaction tube in the fixed-bed multitubular reactor".) made high and in the case of carrying out the reaction with the space velocity made large, or with the concentration of the raw material gas made high, for the purpose of enhancing the productivity of the objective product.

The above problems are explained again below. If attention is directed to the entirety of the catalyst layer as packed in the reaction tube, then the catalyst as located at the hot spot portion causes the oxidation reaction excessively, and besides, this catalyst is more rapidly deteriorated than catalysts as located at the other portions. Particularly in longtime use, the yield of the objective product is greatly lowered, so its production can be difficult to stably carry out.

In order to cope with such problems, there is proposed a process in which it is arranged that the size (occupation volume) of a catalyst packed in a reaction tube should become smaller in order from the side of the inlet of such as raw material gas toward the outlet side (e.g. refer to patent documents 1 and 2 below). There are also its examples industrially carried out.

In addition, there are proposed: a process which involves lowering the supporting ratio of an active component of a catalyst packed on the side of the inlet of such as raw material gas (e.g. refer to patent document 3 below); and a process which involves packing a catalyst of which the activity has been lowered by adding an alkaline metal (e.g. refer to patent document 4 below).

[Patent Document 1] JP-B-084400/1995 (Kokoku)
[Patent Document 2] JP-A-241209/1997 (Kokai)
[Patent Document 3] JP-A-010802/1995 (Kokai)
[Patent Document 4] JP-A-336060/2000 (Kokai).

However, in view of high levels (e.g. high gas pressure conditions) required by recent years' technological progress in point of enhancing the productivity of the objective product, even such prior processes still would not be said to be sufficient to suppress the thermal accumulation (rise of temperature) at the hot spot portion. In addition, even if the use of a catalyst of a larger size (occupation volume) is necessary for making the catalytic activity in a predetermined reaction zone come in a lower range, there is a limitation on the size (length) of the tube diameter of each reaction tube. Therefore, for example, if an attempt is made to pack a catalyst of which the maximum particle diameter is slightly smaller than the tube diameter, then there is a case where the reaction tube could be unfavorably bridged (clogged up) with this catalyst anywhere inside the reaction tube. In such a case, for example, it is difficult to even out the packing amounts of the catalyst in all reaction tubes, so that the yield of the objective product is greatly decreased, or that its quality is widely dispersed.

SUMMARY OF THE INVENTION

A. Object of the Invention

Thus, an object of the present invention is to provide a catalytic gas phase oxidation reaction with molecular oxygen or a molecular-oxygen-containing gas by using a fixed-bed multitubular reactor packed with catalysts, in which: even under reaction conditions of a higher gas pressure, a higher concentration of the raw material gas and a larger space velocity of a reaction gas, the thermal accumulation at the hot spot portion can be sufficiently suppressed with ease and at low costs, so that the reaction can be continued for a long time while a high yield is maintained.

B. Disclosure of the Invention

The present inventors diligently studied in order to solve the above problems. As a result, they have found out that: if, in the case of trying to adjust the catalytic activity in a predetermined reaction zone (particularly, on the gas-inlet side) in order to suppress the thermal accumulation at the hot spot portion, catalysts having different occupation volumes (sizes) are used as conventional and mixed with an inert substance molding (e.g. particles) to dilute the catalyst concentration, then the catalytic activity can be easily and accurately adjusted, without even causing the aforementioned problems, even to a range to which the catalytic activity cannot be adjusted by conventional methods. In addition, if the catalysts having different occupation volumes are prepared to the smallest necessary number of kinds, then the joint use of the inert substance molding makes it possible to set and adjust the catalytic activity, even industrially with ease and at low costs and further in rich variety, even to a subtle range to which the catalytic activity cannot be adjusted by only the occupation volume. The present inventors actually carried out the production of the unsaturated aldehyde and/or unsaturated carboxylic acid by utilizing such points excellent in hardware aspects. As a result, they have succeeded in confirming that: even in a reaction under conditions of a higher gas pressure, a higher concentration of the raw material gas and a larger space velocity of a reaction gas (such a reaction has hitherto had an aspect of being difficult to control), the thermal accumulation at the hot spot portion can be sufficiently suppressed, so that the reaction can be continued for a long time while the deterioration of the catalyst is suppressed to thus maintain a high yield.

The present invention has been completed on the basis of the above findings.

Incidentally, as another technique for suppressing the thermal accumulation at the hot spot portion, there is proposed a process in which a catalyst packed in a reaction tube is diluted with an inert material to thereby arrange that the activity should become higher continuously or stepwise from the gas-inlet side toward the gas-outlet side (e.g. JP-B-030688/1978 (Kokoku)). However, the catalytic gas phase oxidation reaction according to the present invention is not based on such a concept that the thermal accumulation at the hot spot portion is suppressed by making the dilution with the inert material and thereby providing the catalytic activity with a gradient. In detail, since the catalytic gas phase oxidation reaction according to the present invention stands on the assumption of a concept that the catalytic activity is provided with a gradient by stepwise packing the catalyst particles having different occupation volumes and since the catalytic gas phase oxidation reaction according to the present invention adds a technique of the dilution with the inert material further to the technique (based on the above concept) as a means for making this technique (based on the above concept) cope with the aforementioned higher degree of reaction conditions, the catalytic gas phase oxidation reaction according to the present invention is not based on the concept that the catalytic activity is provided with a gradient by the dilution with the inert material.

A catalytic gas phase oxidation reaction according to the present invention is a catalytic gas phase oxidation reaction with molecular oxygen or a molecular-oxygen-containing gas by using a fixed-bed multitubular reactor packed with catalysts; with the catalytic gas phase oxidation reaction being characterized in that: a catalyst-packed layer of each reaction tube of the reactor is divided into at least two reaction zones in a tubular axial direction; and the packing of the catalysts is such that the occupation volumes of the catalysts differ between at least two of the reaction zones and that an inert substance molding is mixed in at least one of the reaction zones.

The above occupation volume of the catalyst refers to a volume of a space occupied by each catalyst particle when the catalyst is packed in the catalyst-packed layer of each reaction tube.

C. Effects of the Invention

The present invention can provide a catalytic gas phase oxidation reaction with molecular oxygen or a molecular-oxygen-containing gas by using a fixed-bed multitubular reactor packed with catalysts, in which: even under reaction conditions of a higher gas pressure, a higher concentration of the raw material gas and a larger space velocity of a reaction gas, the thermal accumulation at the hot spot portion can be sufficiently suppressed with ease and at low costs, so that the reaction can be continued for a long time while a high yield is maintained.

In addition, the catalytic gas phase oxidation reaction according to the present invention can be utilized for a process for production of an unsaturated aldehyde and/or unsaturated carboxylic acid under various conditions and can achieve the stabilization of the yield of the unsaturated aldehyde and/or unsaturated carboxylic acid for a long time, the enhancement of the yield of the unsaturated aldehyde and/or unsaturated carboxylic acid, and the maintenance of the catalyst life time even under reaction conditions other than reaction conditions of a higher gas pressure, a higher concentration of the raw material gas and a larger space velocity of a reaction gas.

These and other objects and the advantages of the present invention will be more fully apparent from the following detailed disclosure.

DETAILED DESCRIPTION OF THE INVENTION

Hereinafter, detailed descriptions are given about the catalytic gas phase oxidation reaction according to the present invention (which may hereinafter be referred to as catalytic gas phase oxidation reaction of the present invention). However, the scope of the present invention is not bound to these descriptions. And other than the following illustrations can also be carried out in the form of appropriate modifications of the following illustrations within the scope not departing from the spirit of the present invention.

It is important that the catalytic gas phase oxidation reaction of the present invention has the aforementioned technical features in the catalytic gas phase oxidation reaction with molecular oxygen or a molecular-oxygen-containing gas by using a fixed-bed multitubular reactor packed with catalysts.

As the catalytic gas phase oxidation reaction of the present invention, specifically, there are preferred the following: (A) a catalytic gas phase oxidation reaction in which at least one compound selected from the group consisting of propylene, isobutylene, t-butyl alcohol, and methyl t-butyl ether is used as a raw material to produce an unsaturated aldehyde (favorably, acrolein) corresponding to the raw material; (B) a catalytic gas phase oxidation reaction in which an unsaturated aldehyde is used as a raw material to produce an unsaturated carboxylic acid corresponding to the raw material (favorably, a catalytic gas phase oxidation reaction in which acrolein is used as a raw material to produce acrylic acid); and (C) a catalytic gas phase oxidation reaction in which at least one compound selected from the group consisting of propylene, isobutylene, t-butyl alcohol, and methyl t-butyl ether is used as a raw material to produce an unsaturated carboxylic acid (favorably, acrylic acid) corresponding to the raw material.

The catalyst usable in the present invention may be a molded type catalyst as obtained by molding a catalytic component alone into a definite shape, or a supported type catalyst as obtained by supporting a catalytic component on any inert support having a definite shape, or a catalyst comprising a combination of these molded type catalyst and supported type catalyst, thus not limited.

As the above catalytic component which is used for the catalyst usable in the present invention, there are favorably used the following oxides and/or composite oxides.

When at least one compound selected from the group consisting of propylene, isobutylene, t-butyl alcohol, and methyl t-butyl ether is used as a raw material to produce an unsaturated aldehyde and/or unsaturated carboxylic acid corresponding to the raw material, then any catalytic component is usable if it is a catalytic component possible to produce the unsaturated aldehyde and/or unsaturated carboxylic acid corresponding to the following raw material by a catalytic gas phase oxidation reaction in which, as the above raw material, there is used the at least one compound selected from the group consisting of propylene, isobutylene, t-butyl alcohol, and methyl t-butyl ether. However, for example, there is favorably used an oxide and/or composite oxide of a general formula (1) below:

$$Mo_aW_bBi_cFe_dA_eB_fC_gD_hO_x \qquad (1)$$

(where: Mo is molybdenum; W is tungsten; Bi is bismuth; Fe is iron; A is at least one element selected from among cobalt and nickel; B is at least one element selected from among boron, phosphorus, chromium, zinc, niobium, tin, antimony, cerium, and lead; C is at least one element selected from among alkaline metals; D is at least one element selected from among silicon, aluminum, titanium, and zirconium; and O is oxygen; and further, a, b, c, d, e, f, g, h, and x denote atomic ratios of Mo, W, Bi, Fe, A, B, C, D, and O respectively; and, in the case of a=12, the following are satisfied: $0 \leq b \leq 5$; $0.1 \leq c \leq 10$; $0.1 \leq d \leq 10$; $1 \leq e \leq 20$; $0 \leq f \leq 5$; $0.001 \leq g \leq 3$; and $0 \leq h \leq 100$; and x is a numerical value as determined by the oxidation state of each element).

When an unsaturated aldehyde is used as a raw material to produce an unsaturated carboxylic acid corresponding to the raw material, then any catalytic component is usable if it is a catalytic component possible to produce the unsaturated carboxylic acid corresponding to the following raw material by a catalytic gas phase oxidation reaction in which, as the above raw material, there is used the unsaturated aldehyde. However, for example, there is favorably used an oxide and/or composite oxide of a general formula (2) below:

$$Mo_aV_bW_cA_dB_eC_fD_gE_hO_x \qquad (2)$$

(where: Mo denotes molybdenum; V denotes vanadium; W denotes tungsten; A denotes at least one element selected from among antimony and tin; B denotes at least one element selected from among copper and iron; C denotes at least one element selected from among magnesium, calcium, strontium, and barium; D denotes at least one element selected from among titanium, zirconium, and cerium; E denotes at least one element selected from among alkaline metals; and O denotes oxygen; and further, a, b, c, d, e, f, g, h, and x denote atomic ratios of Mo, V, W, A, B, C, D, E, and O respectively; and, in the case of a=12, the following are satisfied: b=2–14; c=0–12; d=0–5; e=0–6; f=0–3; g=0–10; and h=0–5; and x is a determined by the oxidation state of each element).

The oxide and/or complex oxide of the above general formula (1) or (2) can be produced by hitherto publicly known processes.

There is no limitation on the starting materials for obtaining the above catalytic components. Ammonium salts, nitrates, carbonates, chlorides, sulfates, hydroxides, organic acid salts, and oxides of metal elements as generally used for this kind of catalyst, or a mixture of these, may be used in combination. However, the ammonium salts and nitrates are favorably used.

A mixed liquid of the starting materials (starting-materials-mixed liquid) may be prepared by processes as generally used for this kind of catalyst. For example, the above starting materials are mixed into water in order, thereby forming an aqueous solution or slurry. In the case where at least two aqueous solutions or slurries are prepared according to the kinds of the starting materials, these aqueous solutions or slurries may be mixed together in order. There is no limitation on the conditions for the mixing (e.g. mixing order, temperature, pressure, and pH) of the starting materials.

The prepared mixed liquid of starting materials is dried by various methods, thus forming a dried material (which may be referred to as catalyst precursor; hereinafter the same). Examples of the above methods include: a drying method by heating; and a drying method under reduced pressure. Above all, as to the heating method for obtaining the dried material and as to the form of the dried material, for example, a powdery dried material may be obtained with such as a spray dryer and a drum dryer, or a blockish or flaky dried material may be obtained by heating under a gas stream with such as a box-type dryer or a tunnel-type dryer. In addition, in the heating method for obtaining the dried material, there is also a case where: the mixed liquid of starting materials is evaporated to dryness (concentrated to dryness) to obtain a cake solid, and then this solid is further heat-treated in the above way. On the other hand, as to the drying method under reduced pressure and as to the form of the dried material, for example, a blockish or powdery dried material may be obtained with such as a vacuum dryer.

The resultant dried material is transferred to the subsequent molding step after having, if necessary, been subjected to a pulverization step and/or a classification step for obtaining a powder having appropriate particle diameters. In addition, before being transferred to the molding step, the resultant dried material may be calcined.

The method for molding the catalysts is free of especial limitation if this method is a method that can form particulate catalysts (including the supported type catalysts) of desired shapes. Hitherto publicly known methods are adoptable. Examples thereof include a tumbling granulation method, an extrusion-molding method (extrusion-molding machine), a tabletting method, Marumerizer method, an impregnating method, an evaporation-to-dryness method, and a spraying method.

In the molding step, such as a liquid binder can be used for molding the dried material (as a catalytic-component precursor) (including supporting the dried material onto the support).

Incidentally, for obtaining the catalysts as used in the present invention, there can be adopted, besides the aforementioned production methods, another method in which: the starting-materials-mixed liquid is used in the form left as it is a liquid without drying it; and this liquid is made to be absorbed by a desired support or coated thereto, thereby supporting the catalytic components onto the support (e.g. evaporation-to-dryness method or spraying method). Accordingly, examples of the method for supporting the catalytic components onto the support include, besides the aforementioned method in which the dried material is supported, another method in which the starting-materials-mixed liquid itself is supported.

There is no especial limitation on the above liquid binder. However, it is possible to use binders as generally used for molding and supporting this kind of catalyst. Specific examples of the usable binders include water, and besides, the following other binders: organic compounds (e.g. ethylene glycol, glycerin, propionic acid, benzyl alcohol, propyl alcohol, polyvinyl alcohol, and phenol); nitric acid; and silica sol. In addition, these may be used either alone respectively or in combinations with each other.

When the catalysts usable in the present invention are obtained, then it is possible to use various substances (e.g. molding assistants capable of enhancing the moldability;

reinforcements for enhancing the catalyst strength; and pore-forming agents for forming adequate pores in the catalyst) as generally used for the purpose of these effects in the production of catalysts. Examples of these various substances include stearic acid, maleic acid, ammonium nitrate, ammonium carbonate, graphite, starch, cellulose, silica, alumina, glass fibers, silicon carbide, and silicon nitride. Favorable are substances of which the addition does not have bad influence on the catalytic performances (e.g.: activity; selectivity of the objective product). These various substances can be used, for example, by adding them to such as the above liquid binder or starting-materials-mixed liquid or its dried material to mix them together. In the case where the amount of the above substances as added is in excess, the physical strength of the catalyst is occasionally remarkably lowered. Therefore it is favorable to add them in such an amount as does not lower the physical strength of the catalyst to such an extent that the catalyst cannot be practically used as an industrial catalyst.

There is no limitation on the shape of the catalyst usable in the present invention, and the shape may be any shape of such as a spherical shape and a columnar shape (pellet shape). Above all, however, the spherical shape and the columnar shape are favorable. The shape of the above catalyst may be a shape further having a hole and is therefore not limited. In the case of the shape further having a hole, the hole may be either a penetrated shape (ring shape) or a concave shape with a bottom, but the penetrated hole is favorable. Needless to say, for example, in the case of the spherical shape, it does not need to be a true sphere, but may be a substantially spherical shape. In this respect, the case of the columnar shape is also similar as to such as its sectional shape. Incidentally, in the case of the spherical shape, if it is a true sphere, then the diameter of this sphere is treated as the diameter D of the corresponding spherical catalyst and, if the above spherical shape is not a true sphere, then the average value of the longest outer diameter and the shortest outer diameter is treated as the diameter D of the corresponding spherical catalyst. In the case of the columnar shape, if its cross section in the direction vertical to the axis (circular axis) has a true circular shape, then the diameter of this true circle is treated as the diameter D of the section of the corresponding columnar catalyst and, if the above cross section of the columnar shape is not a true circular shape, then the average value of the longest outer diameter and the shortest outer diameter is treated as the diameter D of the section of the corresponding columnar catalyst.

Incidentally, in the catalytic gas phase oxidation reaction of the present invention, it is basically arranged that an identical reaction tube should be packed with substantially uniform catalysts as obtained by preparation under set conditions where the resultant catalysts can have the same shape and the same size. As to the shape of the catalyst, this shape in each reaction zone may be either identical with or different from that in another reaction zone (e.g. gas-inlet side: spherical catalyst, and gas-outlet side: columnar catalyst). However, it is favorable to pack the catalysts of the same shape in all the reaction zones.

The "occupation volume" of the catalyst, as referred to in the catalytic gas phase oxidation reaction of the present invention, means a space volume occupied by every one of catalysts (catalyst particles) packed in the catalyst-packed layer (in detail, each reaction zone) of each reaction tube. Incidentally, the occupation volumes of the catalysts (catalyst particles) are determined by the below-mentioned calculation equation according to their shapes. However, in the present invention, when the occupation volumes of the catalysts being packed into a predetermined reaction zone are calculated, they are defined as being determined in the following way: the diameters D and lengths L of all of 100 pieces sampled at random from the catalysts being packed into that reaction zone are beforehand actually measured to calculate their respective average values, and then these average diameter and length are regarded as the diameters D and lengths L of the catalysts being packed into that the reaction zone, thus determining the occupation volumes of those catalysts. This definition is similarly applied also to the below-mentioned detailed description of Examples of some preferred embodiments.

In the case where the catalyst has the spherical shape, its occupation volume (V) can be represented by the following equation:

$$V(mm^3) = (4/3) \times \pi \times (D/2)^3$$

(wherein D (mm) represents the diameter of the spherical catalyst).

Therefore, in the case of the spherical catalyst, the catalysts having different occupation volumes can be prepared by changing the diameter D of the above spherical catalyst.

In the case where the catalyst has the columnar shape, its occupation volume (V) can be represented by the following equation:

$$V(mm^3) = \pi \times (D/2)^2 \times L$$

(wherein: D (mm) represents the diameter of the circular section of the columnar catalyst; and L (mm) represents its axial length).

Therefore, in the case of the columnar catalyst, the catalysts having different occupation volumes can be prepared by changing the diameter D and/or length L of the above columnar catalyst.

In the catalytic gas phase oxidation reaction of the present invention, it is assumed that, even if the shape of the catalyst being used is the aforementioned shape further having a hole, there is no influence on the occupation volume of the above catalyst. The size of the hole (i.e. hole diameter, hole depth, hole volume, etc.) can be set at any value.

As to the above spherical or columnar catalyst, neither of its diameter D and length L is limited. However, both are favorably within the range of 3 to 15 mm, more favorably 4 to 10 mm. When the diameter D and the length L are less than 3 mm, there is a possibility that the catalyst particles may be too small, so the temperature of the hot spot portion may tend to rise. When the diameter D and the length L exceed 15 mm, there is a possibility that the catalyst particles may be too large, so the packing into each reaction tube may be difficult. As to the columnar catalyst, particularly the length L is favorably 0.5 to 2.0 times, more favorably 0.7 to 1.5 times, as long as the diameter D.

In the case where the catalyst used for the catalytic gas phase oxidation reaction of the present invention is the supported type catalyst, any support is usable without limitation on such as its material if that support is a support usually usable when catalysts for catalytic gas phase oxidation reactions are produced. Examples of such a support include supports of definite shapes including such as alumina, silica, silica-alumina, titania, magnesia, silica-magnesia, silica-magnesia-alumina, silicon carbide, silicon nitride and zeolite. As to the case where the shape of the catalyst is the aforementioned shape further having a hole, it is enough to use a support having a hole.

In the case of the supported type catalyst, the supporting ratio of the catalytic component is determined appropriately so that the optimum activity and selectivity can be obtained with consideration given to such as: oxidation reaction conditions; and activity and strength of the catalyst. However, the supporting ratio is favorably within the range of 5 to 95 mass %, more favorably 20 to 90 mass %. Incidentally, in the catalytic gas phase oxidation reaction of the present invention, the supporting ratio of the catalytic component may be either identical or different between the catalyst being packed in each reaction zone and that being packed in another reaction zone, thus not limited. Hereupon, the supporting ratio is defined as a value determined by the following equation.

Supporting ratio (mass %)=[(mass (g) of catalyst obtained−mass (g) of support used)/mass (g) of catalyst obtained]×100

There is no limitation on the heat-treatment conditions (so-called calcination conditions) during the preparation of the catalyst, either. Applicable are calcination conditions which are generally adopted in the production of this kind of catalyst. The heat-treatment temperature is favorably within the range of 350 to 650° C., more favorably 400 to 600° C., in the case of the catalyst used when at least one compound selected from the group consisting of propylene, isobutylene, t-butyl alcohol, and methyl t-butyl ether is used as a raw material to produce an unsaturated aldehyde and/or unsaturated carboxylic acid corresponding to the raw material. In addition, the heat-treatment temperature is favorably within the range of 300 to 500° C., more favorably 350 to 450° C., in the case where an unsaturated aldehyde is used as a raw material to produce an unsaturated carboxylic acid corresponding to the raw material. The heat-treatment time is favorably within the range of 1 to 24 hours, more favorably 3 to 12 hours. Incidentally, in the catalytic gas phase oxidation reaction of the present invention, the above calcination conditions may be either identical or different between the catalyst being packed in each reaction zone and that being packed in another reaction zone, thus not limited.

In the catalytic gas phase oxidation reaction of the present invention, it is important that: the catalyst-packed layer of each reaction tube of the fixed-bed multitubular reactor being used for the reaction is divided into at least two reaction zones in a tubular axial direction; and the catalysts are packed in each of these reaction zones in such a mode that the aforementioned occupation volumes differ between at least two of the above reaction zones; and an inert substance molding is mixed in at least one of the above reaction zones.

There is no limitation on the number of the reaction zones in the catalyst-packed layer. However, industrially, it is favorable to adjust this number to about 2 or about 3, whereby the objective effects can be obtained sufficiently. In addition, as to the dividing ratio (ratio between catalyst-packed layer lengths of reaction zones) of the catalyst-packed layer, its optimum value depends upon such as: oxidation reaction conditions; and composition, shape, and size of the catalyst as packed in each layer. Therefore, the ratio cannot be specified sweepingly. The ratio may appropriately be selected so as to obtain the optimum activity and selectivity as a whole.

In the catalytic gas phase oxidation reaction of the present invention, it is enough that the specific catalyst-packing mode concerning the occupation volumes of the catalysts is, as aforementioned, that the occupation volumes differ between at least two (which may be either adjacent to or apart from each other) of the reaction zones. Thus, there is no limitation on the above mode. Favorable is, however, a mode that the occupation volume of the packed catalyst in a reaction zone nearest the gas-outlet side is smaller than that in a reaction zone nearest the gas-inlet side. And more favorable is a mode that: the occupation volume of the packed catalyst in a reaction zone nearest the gas-outlet side is smaller than that in a reaction zone nearest the gas-inlet side, and the occupation volume of the packed catalyst in a reaction zone on the gas-outlet side is not larger than (i.e. is smaller than or the same as) that in a reaction zone on the gas-inlet side, wherein these reaction zones are any two reaction zones which are adjacent to each other. And still more favorable is a mode that the occupation volume of the packed catalyst becomes smaller in order from the reaction zone nearest the gas-inlet side toward the reaction zone nearest the gas-outlet side. More specifically, for instance, when three reaction zones are made and referred to as a first reaction zone, a second reaction zone, and a third reaction zone from the gas-inlet side toward the gas-outlet side, then the above mode may be as follows: a mode that the occupation volume of the catalyst becomes smaller in order from the first reaction zone toward the third reaction zone; or a mode that the occupation volume of the packed catalyst in the second reaction zone is smaller than that in the first reaction zone, and that the occupation volume of the packed catalyst in the second reaction zone is the same as that in the third reaction zone; or a mode that the occupation volume of the packed catalyst in the first reaction zone is the same as that in the second reaction zone, and that the occupation volume of the packed catalyst in the third reaction zone is smaller than that in the second reaction zone; or a mode that the occupation volume of the packed catalyst in the second reaction zone is larger than that in the first reaction zone, and that the occupation volume of the packed catalyst in the third reaction zone is smaller than that in the second reaction zone, and that the occupation volume of the packed catalyst in the third reaction zone is smaller than that in the first reaction zone; or a mode that the occupation volume of the packed catalyst in the second reaction zone is smaller than that in the first reaction zone, and that the occupation volume of the packed catalyst in the third reaction zone is larger than that in the second reaction zone, and that the occupation volume of the packed catalyst in the third reaction zone is smaller than that in the first reaction zone. There is no limitation thereto.

In the present invention, each reaction zone is favorably in formation lined up in the tubular axial direction of each reaction tube in the fixed-bed multitubular reactor used for the reaction, that is, in formation where the boundary of each reaction zone is arranged in parallel to the section of the reaction tube. However, the present invention is not limited to this formation. For instance, the formation may be such that the boundary of each reaction zone is arranged in a state having a certain angle (in an inclined state) to the section of the reaction tube. In addition, the formation may be such that: a part of the boundary of each reaction zone is arranged in parallel to the section of the reaction tube, the remaining part is arranged in a state having a certain angle (in an inclined state) to the section of the reaction tube.

The above catalyst-packing mode concerning the occupation volumes of the catalysts is particularly favorably that the ratio between occupation volumes of the catalysts in two reaction zones adjacent to each other is adjusted within a specific range. Thereby very excellent effects can be obtained in point of the suppression of the thermal accumulation at the hot spot portion. Specifically, when the occupation volume in the gas-inlet-side one of the two reaction zones adjacent to each other is represented by $V_1$ and that in the gas-outlet-side one is represented by $V_2$, then $V_1/V_2$ is, for example, favorably within the range of 1.2/1 to 64/1, more favorably $V_1/V_2=1.3/1$ to 27/1. When the ratio $(V_1/V_2)$ between the occupation volumes is less than 1.2/1, there is a possibility that the effect of the suppression of the thermal accumulation at the hot spot portion cannot be sufficiently obtained, so the significance of making the reaction zones in numbers may be lost. When the ratio $(V_1/V_2)$ is more than 64/1, there is a possibility that it may become necessary to put up with a low productivity in order to suppress the thermal accumulation at the hot spot portion in the reaction zone smaller in occupation volume, and that the pressure drop in the reaction zones may increase.

In the catalytic gas phase oxidation reaction of the present invention, it is enough that the specific packing mode concerning the mixing of the inert substance molding is, as aforementioned, that the catalyst is mixed with the inert substance molding in at least one of the reaction zones to thereby decrease (dilute) the catalytic activity. Thus, there is no limitation on the above mode. Examples thereof include: a mode that the inert substance molding is mixed in the reaction zone nearest the gas-inlet side; and a mode that the inert substance molding is mixed in all of the reaction zones. Preferable is, however, the mode that the inert substance molding is mixed in the reaction zone nearest the gas-inlet side. More specifically, for instance, when, as aforementioned, the three reaction zones are made and referred to as the first reaction zone, the second reaction zone, and the third reaction zone from the gas-inlet side toward the gas-outlet side, then the reaction zones in which the inert substance molding is mixed may be only the first reaction zone, or may be only the first reaction zone and the second reaction zone, or may be all of the first, second and third reaction zones. Thus, there is no limitation. Favorable is, however, the mode that the inert substance molding is mixed in only the first reaction zone, or the mode that the inert substance molding is mixed in the first reaction zone and the second reaction zone.

As the inert substance molding used in the present invention, any inert substance molding is usable if it is a substance substantially inert upon the reaction gas. Examples thereof include moldings of definite shapes including at least one component selected from among alumina, silica, silica-alumina, zirconia, titania, magnesia, silica-magnesia, silica-magnesia-alumina, silicon carbide, silicon nitride and zeolite, wherein such moldings are used commonly as inert supports.

There is no especial limitation on the shape of the inert substance molding, and the shape may be any shape of such as a spherical shape, a columnar shape (pellet shape), and a ring shape.

The inert substance molding used in the present invention may be either (A) or (B) shown below.

(A) A pulverized material of an inert substance. Specifically, this is a material obtained by a process in which the inert substance is pulverized and then either sieved so as to possess prescribed particle diameters or adjusted so as to be a prescribed shape (e.g. spherical shape).

(B) A material obtained by a process in which: fine particles of the inert substance or a pulverized material of the inert substance is mixed with a paste agent or additive, and then the resultant mixture is molded into such as a support shape (e.g. a spherical shape, a disk shape, a columnar shape, a pellet shape).

As to the inert substance usable in the present invention, there is no especial limitation on such as its production process or shape. As the inert substance molding used in the present invention, the case of (B) above is favorable in that: the shape is uniform, and it is easy to obtain a material of a necessary size and shape, and it becomes possible to carry out packing which facilitates the adjustment of the conditions of the reaction tube.

As to the above spherical or columnar inert substance molding, neither of its diameter D and length L is limited. However, both are favorably within the range of 3 to 15 mm, more favorably 4 to 10 mm. When the diameter D and the length L are less than 3 mm, there is a possibility that the inert substance molding may be too small, so the temperature of the hot spot portion may tend to rise. When the diameter D and the length L exceed 15 mm, there is a possibility that the inert substance molding may be too large, so the packing into each reaction tube may be difficult. As to the columnar inert substance molding, particularly the length L is favorably 0.5 to 2.0 times, more favorably 0.7 to 1.5 times, as long as the diameter D.

The occupation volume of the inert substance molding used in the present invention can be set at any value. However, it is favorably in the range of 20 to 200 volume %, more favorably 30 to 150 volume %, relative to the occupation volume of the catalyst to be mixed.

The shape and size of the inert substance molding used in the present invention may be the shape and size of the aforementioned support usable in the present invention.

As to the packing mode concerning the mixing of the above inert substance molding, the mixing ratio of the inert substance molding is favorably 80 volume % or less, more favorably in the range of 5 to 60 volume %, still more favorably 10 to 50 volume %. When the above mixing ratio exceeds 80 volume %, there is a possibility not only that the activity may decrease so remarkably as to deteriorate the reaction efficiency, but also that the absolute amount of the catalytic component in the reaction tube may decrease too much, thus resulting in unfavorably shortening the catalyst life time. The definition of the mixing ratio of the inert substance molding will be described in the below-mentioned detailed description of Examples of some preferred embodiments.

Incidentally, in the catalytic gas phase oxidation reaction of the present invention, as to the above mixing ratio, the reaction zones in which the inert substance molding is mixed may be either identical with or different from each other. Thus, there is no limitation.

In the catalytic gas phase oxidation reaction of the present invention, another favorable catalyst-packing mode besides the aforementioned one is that, furthermore, the activities of the catalysts as packed in the aforementioned at least two reaction zones differ between these reaction zones. There is no limitation on the process for preparing the above catalysts different as to the activity. Hitherto publicly known preparation processes may be used. However, examples thereof include: a process that involves changing the kind and/or amount of at least one element selected from among alkaline metals (alkaline metals (e.g. Li, Na, K, Rb, Cs) as components C in the catalytic component (1) usable in the present invention and as components E in the catalytic component (2) usable in the present invention); a process that involves changing the supporting ratio; a process that involves changing the calcination temperature; and a process that involves a combination of these processes. Above all, the above process that involves the combination is favorable in points of the catalyst life time and the yield. If at least two catalysts different as to the activity are arranged in the above way, then the thermal accumulation at the hot spot portion can be suppressed, and also the objective product can be obtained with a high selectivity stably for a long time.

There is no limitation on the catalyst-packing mode in the above case where the activities of the catalysts as packed in the at least two reaction zones differ between these reaction zones. However, examples thereof include: a mode in which the packing is performed in such a manner that the activity increases in order from the gas-inlet-side reaction zone toward the gas-outlet-side reaction zone; and a mode in which the packing is performed in such a manner that, from the gas-inlet-side reaction zone toward the gas-outlet-side reaction zone, the activity once decreases and thereafter increases. Preferable is the former mode. In addition, in the latter mode, the packed-layer length in the gas-inlet-side reaction zone (in which the catalyst having the higher activity is packed) is favorably not more than 50%, more favorably not more than 20%, still more favorably not more than 10%, of the overall length of the catalyst-packed layers.

When the catalytic gas phase oxidation reaction of the present invention is carried out, there is no limitation except for adopting the aforementioned mode as the catalyst-packing mode. This reaction can be performed with appropriate adoption of devices, processes and conditions which are used in general. Hereinafter, descriptions are given about such as general catalytic gas phase oxidation reactions and catalytic gas phase oxidation reaction conditions.

The catalytic gas phase reaction of the present invention can be carried out by a conventional one-pass process or recycling process.

As to reaction conditions for the catalytic gas phase oxidation reaction of the present invention, when at least one compound selected from the group consisting of propylene, isobutylene, t-butyl alcohol, and methyl t-butyl ether is used as a raw material to produce an unsaturated aldehyde and/or unsaturated carboxylic acid corresponding to the raw material, then examples of the above reaction conditions include such that a mixed gas (reaction gas) is introduced into each reaction tube to bring the mixed gas into contact with the catalyst to carry out the reaction in the temperature range of 250 to 450° C. at a space velocity of 300 to 5,000 $hr^{-1}$ (STP), wherein the mixed gas includes such as: the at least one compound selected from the group consisting of propylene, isobutylene, t-butyl alcohol, and methyl t-butyl ether as the raw material gas 1 to 10 volume %; oxygen (molecular oxygen) 3 to 20 volume %; water vapor 0 to 60 volume %; and an inert gas (e.g. nitrogen gas, carbon dioxide gas) as a diluent 20 to 80 volume %. When an unsaturated aldehyde is used as a raw material to produce an unsaturated carboxylic acid corresponding to the raw material, then examples of the above reaction conditions include such that a mixed gas (reaction gas) is introduced into each reaction tube to bring the mixed gas into contact with the catalyst to carry out the reaction in the temperature range of 200 to 400° C. at a space velocity of 300 to 5,000 $hr^{-1}$ (STP), wherein the mixed gas includes such as: the unsaturated aldehyde (favorably, acrolein) as the raw material gas 1 to 10 volume %; oxygen (molecular oxygen) 0.5 to 20 volume %; water vapor 0 to 60 volume %; and an inert gas (e.g. nitrogen gas, carbon dioxide gas) as a diluent 20 to 80 volume %.

In the catalytic gas phase oxidation reaction of the present invention, when at least one compound selected from the group consisting of propylene, isobutylene, t-butyl alcohol, and methyl t-butyl ether is used as a raw material to produce an unsaturated carboxylic acid corresponding to the raw material, then, as to a first-step reaction to form an unsaturated aldehyde from the at least one compound selected from the group consisting of propylene, isobutylene, t-butyl alcohol, and methyl t-butyl ether and as to a second-step reaction to form the unsaturated carboxylic acid from the unsaturated aldehyde, it is permitted that: as is illustrated in the below-mentioned detailed description of Examples of some preferred embodiments, the first-step and second-step reactions are carried out with separate reactors respectively, or a catalyst-packed layer for carrying out the first-step reaction and a catalyst-packed layer for carrying out the second-step reaction are disposed in order in one reactor to thus carry out the first-step and second-step reactions.

When the unsaturated aldehyde is used as the raw material to produce the unsaturated carboxylic acid corresponding to the raw material, then it is also possible to use an unsaturated-aldehyde-containing gas (favorably, acrolein-containing gas) obtained by another reaction (e.g. acrolein-containing gas obtained by carrying out a catalytic gas phase oxidation reaction of propylene using a molybdenum-bismuth-iron-containing catalyst), besides the unsaturated aldehyde (favorably, acrolein), as the raw material gas. In this case, for example, the existence of components other than acrolein (which are contained in the acrolein-containing gas obtained by carrying out the catalytic gas phase oxidation reaction of propylene) (specifically, such as by-products (e.g. acetoaldehyde, acetic acid and carbon oxide), unreacted propylene, propane) does not have any influence on the present invention.

The catalytic gas phase oxidation reaction of the present invention can give remarkably favorable results, in comparison with conventional processes, under high-loading reaction conditions that aim at enhancing the productivity, for example, under conditions where: the gas pressure is higher, the concentration of the raw material gas is higher or the space velocity is larger. Particularly, as to the gas pressure, when at least one compound selected from the group consisting of propylene, isobutylene, t-butyl alcohol, and methyl t-butyl ether is used as a raw material to produce an unsaturated aldehyde corresponding to the raw material, then the present invention can be applied favorably to the case where the gas pressure at the gas outlet of each reaction tube in the fixed-bed multitubular reactor (that is, "gas pressure at the gas outlet of the catalyst-packed layer in the reaction tube" and "gas pressure at the gas outlet of the reaction tube") is 0.15 MPa or more in absolute pressure. The present invention can be applied favorably even to the case where the above gas pressure is more severely 0.17 MPa or more, still more severely 0.19 MPa or more, in absolute pressure. In addition, as to the raw-gas concentration, even if it is favorably not smaller than 5 volume % (more favorably not smaller than 7 volume %, still more favorably not smaller than 9 volume %), the object of the present invention can be achieved sufficiently. In addition, when an unsaturated aldehyde is used as a raw material to produce an unsaturated carboxylic acid corresponding to the raw material or when at least one compound selected from the group consisting of propylene, isobutylene, t-butyl alcohol, and methyl t-butyl ether is used as a raw material to produce an unsaturated carboxylic acid corresponding to the raw material, then the present invention can be applied favorably to the case where the gas pressure at the gas outlet of each reaction tube in the fixed-bed multitubular reactor (that is, "gas pressure at the gas outlet of the catalyst-packed layer in the reaction tube" and "gas pressure at the gas outlet of the reaction tube") is 0.13 MPa or more in absolute pressure. The present invention can be applied favorably even to the case where the above gas pressure is more severely 0.15 MPa or more, still more severely 0.17 MPa or more, particularly severely 0.19 MPa or more, in absolute pressure. In addition, as to the raw-gas concentration, even if it is favorably not smaller than 5 volume % (more favorably not smaller than 7 volume %, still more favorably not smaller than 9 volume %), the object of the present invention can be achieved sufficiently.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to them. For convenience, the unit "part(s) by mass" may hereinafter be abbreviated simply to "part(s)".

Measurement and evaluation methods in the following Examples and Comparative Examples are shown below.

<Conversion, Selectivity and Yield>:

Conversion (mol %)=(mols of reacted raw compound/mols of supplied raw compound)×100

Selectivity (mol %)=(mols of produced objective product/mols of reacted raw compound)×100

Yield (mol %)=(mols of produced objective product/mols of supplied raw compound)×100

<Mixing Ratio of Inert Substance Molding>:

(1) A reaction tube (having the same inner diameter as that of an actual reaction tube) and a catalyst, which are used for an actual catalytic gas phase oxidation reaction, are prepared, and only the catalyst is packed at a packing speed at which the catalyst is packed into the actual reaction tube.

(2) The packing density, when only the catalyst is packed, is determined from the layer length of the packed catalyst and the mass of the packed catalyst by the following equation.

Packing density of catalyst only=(mass of packed catalyst)/(sectional area of reaction tube×length of packed layer)

(3) Only the inert substance molding actually used is packed in the same way as of the above packing of only the catalyst, and the packing density of only the inert substance molding is determined by the following equation.

Packing density of inert substance molding only=(mass of packed inert substance molding)/(sectional area of reaction tube×length of packed layer)

(4) The mixing ratio of the inert substance molding is determined from the above-determined packing density of only the catalyst and the above-determined packing density of the inert substance molding by the following equation.

Mixing ratio of inert substance molding (volume %)= [(mass of inert substance molding)/(packing density of inert substance molding only)]/[(mass of inert substance molding)/(packing density of inert substance molding only)+ (mass of catalyst)/(packing density of catalyst only)]×100.

PRODUCTION EXAMPLE 1

A solution (1) was obtained by dissolving 687 parts of cobalt nitrate, 412 parts of nickel nitrate and 191 parts of ferric nitrate into 1000 parts of ion-exchanged water. Separately, a solution (2) was obtained by dissolving 229 parts of bismuth nitrate into an aqueous nitric acid solution comprising 50 parts of concentrated nitric acid and 200 parts of ion-exchanged water.

The solution (1) and the solution (2) were dropwise added in order to a solution (having been obtained by dissolving 1000 parts of ammonium paramolybdate and 64 parts of ammonium paratungstate into 3000 parts of heated ion-exchanged water under stirring to mix them together. Further thereto a solution (having been obtained by dissolving 4.8 parts of potassium nitrate into 50 parts of ion-exchanged water) was added to obtain a slurry.

A dried material was obtained by continuing to heat the resultant slurry while stirring it. Next, this dried material was pulverized, and then ion-exchanged water (as a binder) was added to the resultant powder, and then they were kneaded together for 1 hour. The resultant mixture was extrusion-molded into a ring shape of 6 mm in outer diameter, 2 mm in inner diameter, and 6 mm in length. Next, the resultant molding was calcined under a stream of air at 480° C. for 8 hours, thus obtaining a catalyst (1). The metal element composition (atomic ratio except for oxygen, hereinafter similar) of this catalyst was as follows.

Catalyst (1): $Mo_{12}W_{0.5}Bi_1Fe_1Co_5Ni_3K_{0.1}$

PRODUCTION EXAMPLE 2

A catalyst (2) was obtained in the same way as of Production Example 1 except that the mixture was extrusion-molded into a ring shape of 8 mm in outer diameter, 2 mm in inner diameter, and 8 mm in length in the production process of the catalyst (1) of Production Example 1.

Shown in Table 1 are the catalyst compositions, shapes, catalyst sizes and occupation volumes of the catalysts (1) and (2).

EXAMPLE 1

A catalyst dilution (length of packed layer: 1000 mm) (having been obtained by mixing the catalyst (2) and alumina balls (having an average diameter of 7 mm (occupation volume: 180 mm$^3$)) (as the inert substance molding) in a mixing ratio of 20 volume %) and the catalyst (1) (length of packed layer: 2000 mm) were packed into a stainless-steel-made reaction tube of 25 mm in inner diameter (being heated with a molten nitrate) in order from its gas-inlet side toward its gas-outlet side. That is, the catalyst-packed layer of the reaction tube was divided into two reaction zones, wherein: the gas-inlet-side reaction zone was packed with the dilution of the catalyst (2), and the gas-outlet-side reaction zone was packed with only the catalyst (1).

A catalytic gas phase oxidation reaction of propylene was carried out by introducing a reaction gas of the following composition into the reaction tube in such a manner that the contact time could be 2.3 seconds. Incidentally, the gas pressure at the gas outlet of the reaction tube was adjusted to 0.12 MPa (absolute pressure). The reaction was continuously performed for 8000 hours. Shown in Table 2 are the results of the measurement at passages of 50 hours and of 8000 hours from the start of the reaction.

<Composition of Reaction Gas>:

Propylene: 8 volume %

Oxygen: 14 volume %

Water vapor: 10 volume %

Inert gas such as nitrogen: 68 volume %

Thereupon, only the alumina balls having the average diameter of 7 mm, used for diluting the catalyst (2), were packed into the reaction tube (length of packed layer: 3000 mm), and the same catalytic gas phase oxidation reaction of propylene as described above was carried out. As a result, the conversion of propylene was 0.3 mol %. Therefrom, it was confirmed that the above alumina balls were substantially inert upon the propylene. Also in the following Examples and Comparative Examples, these alumina balls were used as the inert substance molding.

COMPARATIVE EXAMPLE 1

The catalytic gas phase oxidation reaction of propylene was carried out in the same way as of Example 1 except that only the catalyst (2) was packed instead of the catalyst dilution having been obtained by mixing the alumina balls (having the average diameter of 7 mm) and the catalyst (2). Shown in Table 2 are the results of the measurement at passages of 50 hours and of 8000 hours from the start of the reaction.

COMPARATIVE EXAMPLE 2

The catalytic gas phase oxidation reaction of propylene was carried out in the same way as of Example 1 except that, instead of the catalyst dilution having been obtained by mixing the alumina balls (having the average diameter of 7 mm) and the catalyst (2), there was packed a catalyst dilution having been obtained by mixing the above alumina balls and the catalyst (1) in a mixing ratio of 40 volume %. Shown in Table 2 are the results of the measurement at passages of 50 hours and of 8000 hours from the start of the reaction.

EXAMPLE 2

The catalytic gas phase oxidation reaction of propylene was carried out in the same way as of Example 1 except that the gas pressure at the gas outlet of the reaction tube was changed to 0.16 MPa (absolute pressure). Shown in Table 3 are the results of the measurement at passages of 50 hours and of 8000 hours from the start of the reaction.

COMPARATIVE EXAMPLES 3 to 4

The respective catalytic gas phase oxidation reactions of propylene were carried out in the same way as of Comparative Examples 1 and 2 except that the gas pressure at the gas outlet of the reaction tube was changed to 0.16 MPa (absolute pressure). Shown in Table 3 are the results of the measurement at passages of 50 hours and of 8000 hours from the start of the reaction.

EXAMPLE 3

The catalytic gas phase oxidation reaction of propylene was carried out in the same way as of Example 2 except that a catalyst dilution having been obtained by mixing the alumina balls (having the average diameter of 7 mm) and the catalyst (1) in a mixing ratio of 5 volume % was packed instead of the catalyst (1). Shown in Table 3 are the results of the measurement at passages of 50 hours and of 8000 hours from the start of the reaction.

EXAMPLE 4

The catalytic gas phase oxidation reaction of propylene was carried out in the same way as of Example 1 except that the gas pressure at the gas outlet of the reaction tube was changed to 0.20 MPa (absolute pressure). Shown in Table 4 are the results of the measurement at passages of 50 hours and of 8000 hours from the start of the reaction.

COMPARATIVE EXAMPLES 5 to 6

The respective catalytic gas phase oxidation reactions of propylene were carried out in the same way as of Comparative Examples 1 and 2 except that the gas pressure at the gas outlet of the reaction tube was changed to 0.20 MPa (absolute pressure). Shown in Table 4 are the results of the measurement at passages of 50 hours and of 8000 hours from the start of the reaction.

EXAMPLE 5

A catalyst dilution (length of packed layer: 800 mm) (having been obtained by mixing the catalyst (2) and alumina balls (having an average diameter of 7 mm (occupation volume: 180 mm$^3$)) in a mixing ratio of 20 volume %), a catalyst dilution (length of packed layer: 1100 mm) (having been obtained by mixing the catalyst (1) and the above alumina balls in a mixing ratio of 35 volume %), and the catalyst (1) (length of packed layer: 1100 mm) were packed into the same reaction tube as of Example 1 in order from its gas-inlet side toward its gas-outlet side. That is, the catalyst-packed layer of the reaction tube was divided into three reaction zones, wherein: the reaction zone nearest the gas-inlet side (first reaction zone) was packed with the dilution of the catalyst (2), and the reaction zone nearest the gas-outlet side (third reaction zone) was packed with only the catalyst (1), and the reaction zone therebetween (second reaction zone) was packed with the dilution of the catalyst (1).

A catalytic gas phase oxidation reaction of propylene was carried out by introducing a reaction gas of the same composition as of Example 1 into the reaction tube in such a manner that the contact time could be 2.3 seconds. Incidentally, the gas pressure at the gas outlet of the reaction tube was adjusted to 0.20 MPa (absolute pressure). The reaction was continuously performed for 8000 hours. Shown in Table 4 are the results of the measurement at passages of 50 hours and of 8000 hours from the start of the reaction.

EXAMPLE 6

The catalytic gas phase oxidation reaction of propylene was carried out in the same way as of Example 4 except that a catalyst dilution (length of packed layer: 700 mm) (having been obtained by mixing the catalyst (2) and alumina balls (having an average diameter of 10 mm (occupation volume: 524 mm$^3$)) in a mixing ratio of 30 volume %), a catalyst dilution (length of packed layer: 1100 mm) (having been obtained by mixing the catalyst (1) and alumina balls (having an average diameter of 7 mm (occupation volume: 180 mm$^3$)) in a mixing ratio of 30 volume %), and the catalyst (1) (length of packed layer: 1200 mm) were packed in order from the gas-inlet side toward the gas-outlet side. The reaction was continuously performed for 8000 hours. Shown in Table 4 are the results of the measurement at passages of 50 hours and of 8000 hours from the start of the reaction.

Incidentally, only the alumina balls having the average diameter of 10 mm, used for diluting the catalyst (2), were packed at a layer length of 3000 mm into the stainless-steel-made reaction tube of 25 mm in inner diameter, and the same catalytic gas phase oxidation reaction of propylene as of Example 1 (reaction continuation time: 50 hours) was carried out. As a result, the conversion of propylene was 0.2 mol %. Therefrom, it was confirmed that the above alumina balls were substantially inert upon the propylene.

TABLE 1

| Catalyst No. | Catalyst composition | Shape | Catalyst size | | | Occupation volume (mm³) |
|---|---|---|---|---|---|---|
| | | | Outer diameter (mm) | Inner diameter (mm) | Height (mm) | |
| (1) | $Mo_{12}W_{0.5}Bi_1Fe_1Co_5Ni_3K_{0.1}$ | Ring | 6 | 2 | 6 | 170 |
| (2) | $Mo_{12}W_{0.5}Bi_1Fe_1Co_5Ni_3K_{0.1}$ | Ring | 8 | 2 | 8 | 402 |

TABLE 2

| | Catalyst packing method (gas-inlet side → gas-outlet side) | Reaction continuation time (hours) | Reaction temperature (° C.) | Hot spot temperature (° C.) | Conversion of propylene (mol %) | Total selectivity of (acrolein + acrylic acid) (mol %) | Selectivity of acrylic acid (mol %) | Selectivity of acrolein (mol %) | Total yield of (acrolein + acrylic acid) (mol %) | Yield of acrylic acid (mol %) | Yield of acrolein (mol %) |
|---|---|---|---|---|---|---|---|---|---|---|---|
| Example 1 | Catalyst (2) dilution (mixing ratio: 20 volume %)/ catalyst (1) = 1000 mm/ 2000 mm | 50<br>8000 | 318<br>338 | 374<br>385 | 98.0<br>98.1 | 94.5<br>94.8 | 11.8<br>10.8 | 82.7<br>84.0 | 92.6<br>93.0 | 11.6<br>10.6 | 81.0<br>82.4 |
| Comparative Example 1 | Catalyst (2)/ catalyst (1) = 1000 mm/ 2000 mm | 50<br>8000 | 315<br>339 | 377<br>389 | 98.0<br>97.9 | 94.2<br>94.6 | 12.1<br>11.2 | 82.1<br>83.4 | 92.3<br>92.6 | 11.9<br>11.0 | 80.4<br>81.6 |
| Comparative Example 2 | Catalyst (2) dilution (mixing ratio: 40 volume %)/ catalyst (1) = 1000 mm/ 2000 mm | 50<br>8000 | 315<br>342 | 390<br>404 | 97.9<br>98.0 | 93.9<br>94.2 | 14.1<br>12.3 | 79.8<br>81.9 | 91.9<br>92.3 | 13.8<br>12.1 | 78.1<br>80.2 |

TABLE 3

| | Catalyst packing method (gas-inlet side → gas-outlet side) | Reaction continuation time (hours) | Reaction temperature (° C.) | Hot spot temperature (° C.) | Conversion of propylene (mol %) | Total selectivity of (acrolein + acrylic acid) (mol %) | Selectivity of acrylic acid (mol %) | Selectivity of acrolein (mol %) | Total yield of (acrolein + acrylic acid) (mol %) | Yield of acrylic acid (mol %) | Yield of acrolein (mol %) |
|---|---|---|---|---|---|---|---|---|---|---|---|
| Example 2 | Catalyst (2) dilution (mixing ratio: 20 volume %)/ catalyst (1) = 1000 mm/ 2000 mm | 50<br>8000 | 313<br>328 | 380<br>389 | 98.1<br>98.1 | 94.1<br>94.5 | 12.1<br>11.0 | 82.0<br>83.5 | 92.3<br>92.7 | 11.9<br>10.8 | 80.4<br>81.9 |
| Comparative Example 3 | Catalyst (2)/ catalyst (1) = 1000 mm/ 2000 mm | 50<br>8000 | 310<br>331 | 384<br>401 | 97.8<br>98.1 | 93.6<br>93.8 | 13.0<br>11.9 | 80.6<br>81.9 | 91.5<br>92.0 | 12.7<br>11.7 | 78.8<br>80.3 |
| Comparative Example 4 | Catalyst (1) dilution (mixing ratio: 40 volume %)/ catalyst (1) = 1000 mm/ 2000 mm | 50<br>8000 | 310<br>335 | 398<br>419 | 97.9<br>98.0 | 92.9<br>93.1 | 14.9<br>13.1 | 78.0<br>80.0 | 90.9<br>91.2 | 14.6<br>12.8 | 76.3<br>78.4 |
| Example 3 | Catalyst (2) dilution (mixing ratio: 20 volume %)/ catalyst (1) | 50<br>8000 | 316<br>332 | 386<br>395 | 98.1<br>97.9 | 93.9<br>94.3 | 12.3<br>11.2 | 81.6<br>83.1 | 92.1<br>92.3 | 12.1<br>11.0 | 80.0<br>81.3 |

TABLE 3-continued

| Catalyst packing method (gas-inlet side → gas-outlet side) | Reaction continuation time (hours) | Reaction temperature (° C.) | Hot spot temperature (° C.) | Conversion of propylene (mol %) | Total selectivity of (acrolein + acrylic acid) (mol %) | Selectivity of acrylic acid (mol %) | Selectivity of acrolein (mol %) | Total yield of (acrolein + acrylic acid) (mol %) | Yield of acrylic acid (mol %) | Yield of acrolein (mol %) |
|---|---|---|---|---|---|---|---|---|---|---|
| dilution (mixing ratio: 5 volume %) = 1000 mm/ 2000 mm | | | | | | | | | | |

TABLE 4

| | Catalyst packing method (gas-inlet side → gas-outlet side) | Reaction continuation time (hours) | Reaction temperature (° C.) | Hot spot temperature (° C.) | Conversion of propylene (mol %) | Total selectivity of (acrolein + acrylic acid) (mol %) | Selectivity of acrylic acid (mol %) | Selectivity of acrolein (mol %) | Total yield of (acrolein + acrylic acid) (mol %) | Yield of acrylic acid (mol %) | Yield of acrolein (mol %) |
|---|---|---|---|---|---|---|---|---|---|---|---|
| Example 4 | Catalyst (2) dilution (mixing ratio: 20 volume %)/ catalyst (1) = 1000 mm/ 2000 mm | 50 8000 | 305 316 | 383 395 | 98.3 98.1 | 92.7 93.5 | 12.6 11.5 | 80.1 82.0 | 91.1 91.7 | 12.4 11.3 | 78.7 80.4 |
| Comparative Example 5 | Catalyst (2)/ catalyst (1) = 1000 mm/ 2000 mm | 50 50 8000 | 305 300 318 | — 399 411 | Hot spot temperature remarkably rose, so reaction was given up. 98.5 91.0 14.2 76.8 89.6 14.0 75.6 98.2 91.5 12.9 78.6 89.9 12.7 77.2 | | | | | | |
| Comparative Example 6 | Catalyst (1) dilution (mixing ratio: 40 volume %)/ catalyst (1) = 1000 mm/ 2000 mm | 50 50 8000 | 305 300 321 | — 404 417 | Hot spot temperature remarkably rose, so reaction was given up. 98.5 90.6 16.1 74.5 89.2 15.9 73.3 98.1 91.1 13.3 77.8 89.4 13.0 76.4 | | | | | | |
| Example 5 | Catalyst (2) dilution (mixing ratio: 20 volume %)/ catalyst (1) dilution (mixing ratio: 35 volume %)/ catalyst (1) = 800 mm/ 1100 mm/ 1100 mm | 50 8000 | 307 320 | 382 400 | 98.0 97.9 | 93.1 93.7 | 12.1 11.0 | 81.0 82.7 | 91.2 91.7 | 11.9 10.8 | 79.3 80.9 |
| Example 6 | Catalyst (2) dilution (mixing ratio: 30 volume %)/ catalyst (1) dilution (mixing ratio: 30 volume %)/ catalyst (1) = 700 mm/ 1100 mm/ 1200 mm | 50 8000 | 305 313 | 380 391 | 97.9 98.2 | 93.5 93.6 | 11.9 10.9 | 81.6 82.7 | 91.5 91.9 | 11.7 10.7 | 79.8 81.2 |

PRODUCTION EXAMPLE 3

While 4000 parts of ion-exchanged water was heat-stirred, 600 parts of ammonium paramolybdate, 166 parts of ammonium metavanadate, and 122 parts of ammonium paratungstate were dissolved thereinto.

Separately, while 500 parts of ion-exchanged water was heat-stirred, 178 parts of cupric nitrate and 4 parts of antimony trioxide were added thereinto.

After the resultant two liquids had been mixed together, the resultant mixed liquid was put into a porcelain evaporator on a hot water bath. Then, 2000 parts of a silica-alumina-made support having an average diameter of 5 mm was added to the above mixed liquid. Then, the liquid was evaporated to dryness while stirred to make its dried material adhere to the support. Then, they were calcined at 400° C. for 6 hours, thus obtaining a catalyst (3).

The metal element composition (atomic ratio except for oxygen, hereinafter similar) of this catalyst (3) was as follows.

Catalyst (3): $Mo_{12}V_5W_{1.6}Cu_{2.6}Sb_{0.1}$

PRODUCTION EXAMPLE 4

A catalyst (4) was obtained in the same way as of Production Example 3 except that a silica-alumina-made support having an average diameter of 10 mm was used in place of the silica-alumina-made support having the average diameter of 5 mm in the production process of the catalyst (3) of Production Example 3.

Shown in Table 5 are the catalyst compositions, shapes, catalytic component supporting ratios, catalyst sizes and occupation volumes of the catalysts (3) and (4).

COMPARATIVE EXAMPLE 7

The catalysts (4) and (3) were packed at layer lengths of 1000 mm and 2000 mm respectively into a stainless-steel-made reaction tube of 25 mm in inner diameter (being heated with a molten nitrate) in order from its reaction-gas-inlet side toward its reaction-gas-outlet side.

A catalytic gas phase oxidation reaction of acrolein was carried out by introducing a reaction gas of the following composition into the reaction tube in such a manner that the contact time could be 2.3 seconds. Incidentally, the gas pressure at the gas outlet of the reaction tube was adjusted to 0.11 MPa (absolute pressure). The reaction was continuously performed for 8000 hours. Shown in Table 6 are the results of the measurement at passages of 50 hours and of 8000 hours from the start of the reaction.

<Composition of Reaction Gas>:
Acrolein: 6 volume %
Oxygen: 10 volume %
Water vapor: 10 volume %
Inert gas such as nitrogen: 74 volume %

COMPARATIVE EXAMPLE 8

The catalytic gas phase oxidation reaction of acrolein was carried out in the same way as of Comparative Example 7 except that a catalyst dilution having been obtained by mixing the alumina balls (having an average diameter of 7 mm (occupation volume: 180 mm$^3$)) (as the inert substance molding) and the catalyst (3) in a mixing ratio of 40 volume % was packed instead of the catalyst (4) (that is, the dilution of the catalyst (3) was packed on the reaction-gas-inlet side, and only the catalyst (3) was packed on the reaction-gas-outlet side). Shown in Table 6 are the results of the measurement at passages of 50 hours and of 8000 hours from the start of the reaction.

Incidentally, only the alumina balls having the average diameter of 7 mm, used for diluting the catalyst (3), were packed at a layer length of 3000 mm into the stainless-steel-made reaction tube of 25 mm in inner diameter, and the same catalytic gas phase oxidation reaction of acrolein as of Comparative Example 7 (reaction continuation time: 50 hours) was carried out. As a result, the conversion of acrolein was 0.3 mol %. Therefrom, it was confirmed that the above alumina balls were substantially inert upon the acrolein. Also in the following Examples and Comparative Examples, these alumina balls were used as the inert substance molding.

EXAMPLE 7

The catalytic gas phase oxidation reaction of acrolein was carried out in the same way as of Comparative Example 7 except that a catalyst dilution having been obtained by mixing the alumina balls (having an average diameter of 7 mm) and the catalyst (4) in a mixing ratio of 20 volume % was packed instead of the catalyst (4) (that is, the dilution of the catalyst (4) was packed on the reaction-gas-inlet side, and only the catalyst (3) was packed on the reaction-gas-outlet side). Shown in Table 6 are the results of the measurement at passages of 50 hours and of 8000 hours from the start of the reaction.

COMPARATIVE EXAMPLES 9 to 10

The respective catalytic gas phase oxidation reactions of acrolein were carried out in the same way as of Comparative Examples 7 to 8 except that the gas pressure at the gas outlet of the reaction tube was changed to 0.14 MPa (absolute pressure).

Shown in Table 7 are the results of the measurement at passages of 50 hours and of 8000 hours from the start of the reaction.

EXAMPLE 8

The catalytic gas phase oxidation reaction of acrolein was carried out in the same way as of Example 7 except that the gas pressure at the gas outlet of the reaction tube was changed to 0.14 MPa (absolute pressure). Shown in Table 7 are the results of the measurement at passages of 50 hours and of 8000 hours from the start of the reaction.

EXAMPLE 9

The catalytic gas phase oxidation reaction of acrolein was carried out in the same way as of Example 8 except that a catalyst dilution having been obtained by mixing the alumina balls (having an average diameter of 7 mm) and the catalyst (3) in a mixing ratio of 5 volume % was packed instead of the catalyst (3) (that is, the dilution of the catalyst (4) was packed on the reaction-gas-inlet side, and the dilution of the catalyst (3) was packed on the reaction-gas-outlet side). Shown in Table 7 are the results of the measurement at passages of 50 hours and of 8000 hours from the start of the reaction.

COMPARATIVE EXAMPLES 11 to 12

The respective catalytic gas phase oxidation reactions of acrolein were carried out in the same way as of Comparative Examples 7 to 8 except that the gas pressure at the gas outlet of the reaction tube was changed to 0.18 MPa (absolute pressure).

Shown in Table 8 are the results of the measurement at passages of 50 hours and of 8000 hours from the start of the reaction.

EXAMPLE 10

The catalytic gas phase oxidation reaction of acrolein was carried out in the same way as of Example 7 except that the gas pressure at the gas outlet of the reaction tube was changed to 0.18 MPa (absolute pressure). Shown in Table 8 are the results of the measurement at passages of 50 hours and of 8000 hours from the start of the reaction.

EXAMPLE 11

The catalytic gas phase oxidation reaction of acrolein was carried out in the same way as of Example 10 except that a catalyst dilution (length of packed layer: 800 mm) (having been obtained by mixing the catalyst (4) and alumina balls (having an average diameter of 7 mm) in a mixing ratio of 20 volume %), a catalyst dilution (length of packed layer: 1100 mm) (having been obtained by mixing the catalyst (3) and the above alumina balls in a mixing ratio of 35 volume %), and the catalyst (3) (length of packed layer: 1100 mm) were packed in order from the reaction-gas-inlet side toward the reaction-gas-outlet side. That is, the catalyst-packed layer of the reaction tube was divided into three reaction zones, wherein: the reaction zone nearest the gas-inlet side (first reaction zone) was packed with the dilution of the catalyst (4), and the reaction zone nearest the gas-outlet side (third reaction zone) was packed with only the catalyst (3), and the reaction zone therebetween (second reaction zone) was packed with the dilution of the catalyst (3).

Shown in Table 8 are the results of the measurement at passages of 50 hours and of 8000 hours from the start of the reaction.

EXAMPLE 12

The catalytic gas phase oxidation reaction of acrolein was carried out in the same way as of Example 10 except that a catalyst dilution (length of packed layer: 700 mm) (having been obtained by mixing the catalyst (4) and alumina balls (having an average diameter of 10 mm) in a mixing ratio of 30 volume %), a catalyst dilution (length of packed layer: 1100 mm) (having been obtained by mixing the catalyst (3) and alumina balls (having an average diameter of 7 mm) in a mixing ratio of 30 volume %), and the catalyst (3) (length of packed layer: 1200 mm) were packed in order from the reaction-gas-inlet side toward the reaction-gas-outlet side. That is, the catalyst-packed layer of the reaction tube was divided into three reaction zones, wherein: the reaction zone nearest the gas-inlet side (first reaction zone) was packed with the dilution of the catalyst (4), and the reaction zone nearest the gas-outlet side (third reaction zone) was packed with only the catalyst (3), and the reaction zone therebetween (second reaction zone) was packed with the dilution of the catalyst (3).

Shown in Table 8 are the results of the measurement at passages of 50 hours and of 8000 hours from the start of the reaction.

Incidentally, only the alumina balls having the average diameter of 10 mm, used for diluting the catalyst (4), were packed at a layer length of 3000 mm into the stainless-steel-made reaction tube of 25 mm in inner diameter, and the same catalytic gas phase oxidation reaction of acrolein as of Comparative Example 7 (reaction continuation time: 50 hours) was carried out. As a result, the conversion of acrolein was 0.4 mol %. Therefrom, it was confirmed that the above alumina balls were substantially inert upon the acrolein.

EXAMPLE 13

A catalyst dilution (length of packed layer: 700 mm) (having been obtained by mixing the catalyst (2) and alumina balls (having an average diameter of 7 mm (occupation volume: 180 $mm^3$)) (as the inert substance molding) in a mixing ratio of 30 volume %), the catalyst (2) (length of packed layer: 1100 mm), and the catalyst (1) (length of packed layer: 1200 mm) were packed into a stainless-steel-made reaction tube of 25 mm in inner diameter (being heated with a molten nitrate) in order from its reaction-gas-inlet side toward its reaction-gas-outlet side.

A catalytic gas phase oxidation reaction of propylene was carried out by introducing a reaction gas of the following composition into the reaction tube in such a manner that the contact time could be 2.3 seconds.

<Composition of Reaction Gas>:
Propylene: 8 volume %
Oxygen: 15 volume %
Water vapor: 10 volume %
Inert gas such as nitrogen: 67 volume %

The resultant reaction gas was introduced into a stainless-steel-made reaction tube of 25 mm in inner diameter (being heated with a molten nitrate) packed with a catalyst dilution (length of packed layer: 700 mm) (having been obtained by mixing the catalyst (4) and alumina balls (having an average diameter of 7 mm (occupation volume: 180 $mm^3$)) (as the inert substance molding) in a mixing ratio of 25 volume %), the catalyst (4) (length of packed layer: 1100 mm), and the catalyst (3) (length of packed layer: 1200 mm) in order from the reaction-gas-inlet side toward reaction-gas-outlet side of the reaction tube.

Incidentally, the gas pressure at the gas outlet of the reaction tube was adjusted to 0.20 MPa (absolute pressure). The reaction was continuously performed for 8000 hours. Shown in Table 9 are the results of the measurement at passages of 50 hours and of 8000 hours from the start of the reaction.

TABLE 5

| Catalyst No. | Catalyst composition | Shape | Catalytic component supporting ratio (wt %) | Catalyst size Diameter (mm) | Occupation volume ($mm^3$) |
|---|---|---|---|---|---|
| (3) | $Mo_{12}V_{5.0}W_{1.6}Cu_{2.6}Sb_{0.1}$ | Sphere | 25.2 | 5 | 65 |
| (4) | $Mo_{12}V_{5.0}W_{1.6}Cu_{2.6}Sb_{0.1}$ | Sphere | 25.2 | 10 | 524 |

TABLE 6

| | Catalyst packing method (gas-inlet side → gas-outlet side) | Reaction continuation time (hours) | Reaction temperature (° C.) | Hot spot temperature (° C.) | Conversion of acrolein (mol %) | Selectivity of acrylic acid (mol %) | Yield of acrylic acid (mol %) |
|---|---|---|---|---|---|---|---|
| Comparative Example 7 | Catalyst (4)/catalyst (3) = 1000 mm/2000 mm | 50 | 258 | 317 | 99.0 | 94.8 | 93.9 |
| | | 8000 | 272 | 307 | 99.1 | 94.5 | 93.6 |

TABLE 6-continued

| | Catalyst packing method (gas-inlet side → gas-outlet side) | Reaction continuation time (hours) | Reaction temperature (° C.) | Hot spot temperature (° C.) | Conversion of acrolein (mol %) | Selectivity of acrylic acid (mol %) | Yield of acrylic acid (mol %) |
|---|---|---|---|---|---|---|---|
| Comparative Example 8 | Catalyst (3) dilution (mixing ratio: 40 volume %)/catalyst (3) = 1000 mm/2000 mm | 50<br>8000 | 258<br>275 | 322<br>316 | 98.7<br>98.9 | 94.4<br>94.2 | 93.2<br>93.2 |
| Example 7 | Catalyst (4) dilution (mixing ratio: 20 volume %)/catalyst (3) = 1000 mm/2000 mm | 50<br>8000 | 260<br>270 | 314<br>301 | 99.2<br>99.3 | 95.2<br>95.0 | 94.4<br>94.3 |

TABLE 7

| | Catalyst packing method (gas-inlet side → gas-outlet side) | Reaction continuation time (hours) | Reaction temperature (° C.) | Hot spot temperature (° C.) | Conversion of acrolein (mol %) | Selectivity of acrylic acid (mol %) | Yield of acrylic acid (mol %) |
|---|---|---|---|---|---|---|---|
| Comparative Example 9 | Catalyst (4)/catalyst (3) = 1000 mm/2000 mm | 50<br>8000 | 253<br>265 | 324<br>304 | 99.1<br>98.9 | 94.1<br>93.8 | 93.3<br>92.8 |
| Comparative Example 10 | Catalyst (3) dilution (mixing ratio: 40 volume %)/catalyst (3) = 1000 mm/2000 mm | 50<br>8000 | 253<br>268 | 331<br>318 | 98.9<br>98.7 | 93.5<br>93.3 | 92.5<br>92.1 |
| Example 8 | Catalyst (4) dilution (mixing ratio: 20 volume %)/catalyst (3) = 1000 mm/2000 mm | 50<br>8000 | 254<br>262 | 315<br>299 | 99.4<br>99.2 | 94.7<br>94.8 | 94.1<br>94.0 |
| Example 9 | Catalyst (4) dilution (mixing ratio: 20 volume %)/catalyst (3) dilution (mixing ratio: 5 volume %) = 1000 mm/2000 mm | 50<br>8000 | 256<br>266 | 321<br>305 | 99.3<br>99.5 | 95.0<br>94.8 | 94.3<br>94.3 |

TABLE 8

| | Catalyst packing method (gas-inlet side → gas-outlet side) | Reaction continuation time (hours) | Reaction temperature (° C.) | Hot spot temperature (° C.) | Conversion of acrolein (mol %) | Selectivity of acrylic acid (mol %) | Yield of acrylic acid (mol %) |
|---|---|---|---|---|---|---|---|
| Comparative Example 11 | Catalyst (4)/catalyst (3) = 1000 mm/2000 mm | 50<br>50<br>8000 | 250<br>245<br>256 | Hot spot temperature remarkably rose, so reaction was given up.<br>334<br>315 | <br>99.0<br>99.1 | <br>92.9<br>93.0 | <br>92.0<br>92.2 |
| Comparative Example 12 | Catalyst (3) dilution (mixing ratio: 40 volume %)/catalyst (3) = 1000 mm/2000 mm | 50<br>50<br>8000 | 250<br>245<br>257 | Hot spot temperature remarkably rose, so reaction was given up.<br>346<br>320 | <br>98.8<br>98.7 | <br>91.7<br>92.0 | <br>90.6<br>90.8 |
| Example 10 | Catalyst (4) dilution (mixing ratio: 20 volume %)/catalyst (3) = 1000 mm/2000 mm | 50<br>8000 | 248<br>255 | 318<br>303 | 99.3<br>99.0 | 94.3<br>94.4 | 93.6<br>93.5 |
| Example 11 | Catalyst (4) dilution (mixing ratio: 20 volume %)/catalyst (3) dilution (mixing ratio: 35 volume %)/catalyst (3) = 800 mm/1100 mm/1100 mm | 50<br>8000 | 251<br>260 | 313<br>304 | 99.2<br>99.4 | 94.5<br>94.3 | 93.7<br>93.7 |
| Example 12 | Catalyst (4) dilution (mixing ratio: 30 volume %)/catalyst (3) dilution (mixing ratio: 30 volume %)/catalyst (3) = 700 mm/1100 mm/1200 mm | 50<br>8000 | 250<br>258 | 315<br>304 | 99.4<br>99.3 | 94.4<br>94.2 | 93.8<br>93.5 |

TABLE 9

| | | Catalyst packing method (gas-inlet side → gas-outlet side) | Reaction continuation time (hours) | Reaction temperature of first reactor (° C.) | Reaction temperature of second reactor (° C.) | Hot spot temperature of first reactor (° C.) | Hot spot temperature of second reactor (° C.) | Conversion of propylene (mol %) | Selectivity of acrylic acid (mol %) | Yield of acrylic acid (mol %) |
|---|---|---|---|---|---|---|---|---|---|---|
| Example 13 | First reactor | Catalyst (2) dilution (mixing ratio: 30 volume %)/catalyst (2)/catalyst (1) = 700 mm/ 1100 mm/ 1200 mm | 50 | 306 | 249 | 382 | 315 | 98.0 | 88.5 | 86.7 |
| | Second reactor | Catalyst (4) dilution (mixing ratio: 25 volume %)/catalyst (4)/catalyst (3) = 700 mm/ 1100 mm/ 1200 mm | 8000 | 314 | 256 | 390 | 306 | 98.1 | 88.2 | 86.5 |

INDUSTRIAL APPLICATION

The catalytic gas phase oxidation reaction of the present invention is favorable when a catalytic gas phase oxidation reaction with molecular oxygen or a molecular-oxygen-containing gas by using a fixed-bed multitubular reactor packed with catalysts is carried out.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A catalytic gas phase oxidation reaction, which is a catalytic gas phase oxidation reaction with molecular oxygen or a molecular-oxygen-containing gas by using a fixed-bed multitubular reactor packed with catalysts; wherein:
  a catalyst-packed layer of each reaction tube of the reactor is divided into at least two reaction zones in a tubular axial direction; and
  the packing of the catalysts is such that the occupation volumes of the catalysts differ between at least two of the reaction zones and that the catalysts are mixed with an inert substance molding in at least one of the reaction zones.

2. A catalytic gas phase oxidation reaction according to claim 1, wherein the packing of the catalysts is such that the occupation volume in a reaction zone nearest the gas-outlet side is smaller than that in a reaction zone nearest the gas-inlet side.

3. A catalytic gas phase oxidation reaction according to claim 2, wherein the packing of the catalysts is such that the occupation volume becomes smaller in order from the reaction zone nearest the gas-inlet side toward the reaction zone nearest the gas-outlet side.

4. A catalytic gas phase oxidation reaction according to claim 1, which uses at least one compound selected from the group consisting of propylene, isobutylene, t-butyl alcohol, and methyl t-butyl ether as a raw material to produce an unsaturated aldehyde corresponding to the raw material.

5. A catalytic gas phase oxidation reaction according to claim 4, wherein the gas pressure at the gas outlet of each reaction tube in the reactor is 0.15 MPa or more in absolute pressure.

6. A catalytic gas phase oxidation reaction according to claim 1, which uses an unsaturated aldehyde as a raw material to produce an unsaturated carboxylic acid corresponding to the raw material.

7. A catalytic gas phase oxidation reaction according to claim 6, wherein the gas pressure at the gas outlet of each reaction tube in the reactor is 0.13 MPa or more in absolute pressure.

8. A catalytic gas phase oxidation reaction according to claim 1, which uses at least one compound selected from the group consisting of propylene, isobutylene, t-butyl alcohol, and methyl t-butyl ether as a raw material to produce an unsaturated carboxylic acid corresponding to the raw material.

9. A catalytic gas phase oxidation reaction according to claim 8, wherein the gas pressure at the gas outlet of each reaction tube in the reactor is 0.13 MPa or more in absolute pressure.

10. A catalytic gas phase oxidation reaction according to claim 1, wherein the inert substance molding is mixed with the catalysts after the catalysts have been calcined.

11. A catalytic gas phase oxidation reaction according to claim 1, wherein the inert substance molding is mixed with the catalysts after the catalysts have been molded.

12. A catalytic gas phase oxidation reaction according to claim 1, wherein the inert substance molding is mixed with the catalysts after the catalysts have been rendered in a final shape.

* * * * *